United States Patent
Lampinen

(10) Patent No.: US 8,974,383 B2
(45) Date of Patent: Mar. 10, 2015

(54) PATIENT MONITOR

(75) Inventor: Janne Lampinen, Espoo (FI)

(73) Assignee: General Electric Company, Schenectady, NY (US)

(*) Notice: Subject to any disclaimer, the term of this patent is extended or adjusted under 35 U.S.C. 154(b) by 2273 days.

(21) Appl. No.: 11/550,321

(22) Filed: Oct. 17, 2006

(65) Prior Publication Data

US 2007/0118025 A1 May 24, 2007

(30) Foreign Application Priority Data

Oct. 17, 2005 (EP) .................................... 05109627

(51) Int. Cl.
*A61B 5/00* (2006.01)

(52) U.S. Cl.
CPC . *A61B 5/00* (2013.01); *A61B 5/742* (2013.01); *A61B 2560/0443* (2013.01); *A61B 2562/225* (2013.01)
USPC ....................................................... 600/300

(58) Field of Classification Search
None
See application file for complete search history.

(56) References Cited

U.S. PATENT DOCUMENTS

| | | | | |
|---|---|---|---|---|
| 5,566,048 A | * | 10/1996 | Esterberg et al. | 361/679.27 |
| 6,083,156 A | * | 7/2000 | Lisiecki | 600/301 |
| 6,137,468 A | * | 10/2000 | Martinez et al. | 345/649 |
| 6,188,407 B1 | | 2/2001 | Smith et al. | |
| 6,409,661 B1 | | 6/2002 | Murphy | |
| 6,575,904 B2 | * | 6/2003 | Nagai et al. | 600/301 |
| 6,798,649 B1 | * | 9/2004 | Olodort et al. | 361/679.13 |
| 6,850,784 B2 | * | 2/2005 | SanGiovanni | 455/575.1 |
| 7,025,274 B2 | * | 4/2006 | Solomon et al. | 235/472.01 |
| 7,065,208 B2 | * | 6/2006 | Tsubai et al. | 379/428.03 |
| 7,428,432 B2 | * | 9/2008 | Ali et al. | 600/323 |
| 7,565,182 B2 | * | 7/2009 | Kim | 455/575.1 |
| 8,606,339 B2 | * | 12/2013 | Miyata et al. | 455/575.3 |
| 2001/0047126 A1 | * | 11/2001 | Nagai et al. | 600/300 |
| 2002/0115912 A1 | | 8/2002 | Muraki et al. | |
| 2003/0064685 A1 | * | 4/2003 | Kim | 455/90 |
| 2003/0197679 A1 | * | 10/2003 | Ali et al. | 345/158 |
| 2004/0186357 A1 | * | 9/2004 | Soderberg et al. | 600/300 |

* cited by examiner

*Primary Examiner* — William Thomson
*Assistant Examiner* — Shirley Jian
(74) *Attorney, Agent, or Firm* — GE Global Patent Operation; Marc A. Vivenzio

(57) ABSTRACT

A patient monitor comprising a display means and a parameter connection unit, the parameter connection unit comprising parameter connectors for connecting cables from a patient to the patient monitor. The parameter connection unit is turnably pivoted to the display means.

6 Claims, 2 Drawing Sheets

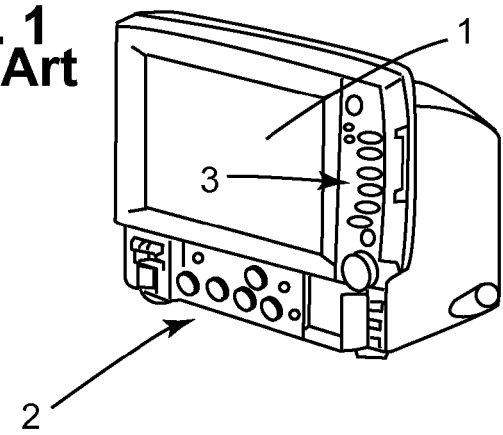
FIG. 1
Prior Art
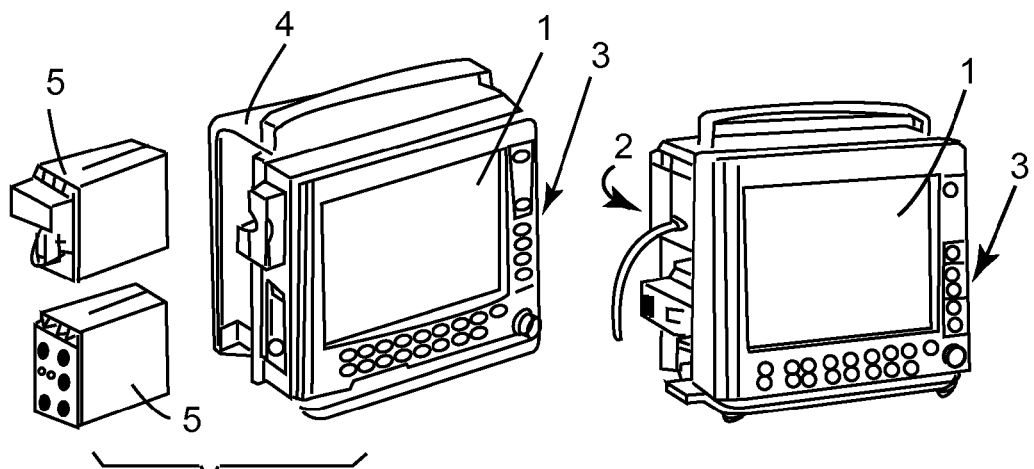
FIG. 2
Prior Art
FIG. 3
Prior Art
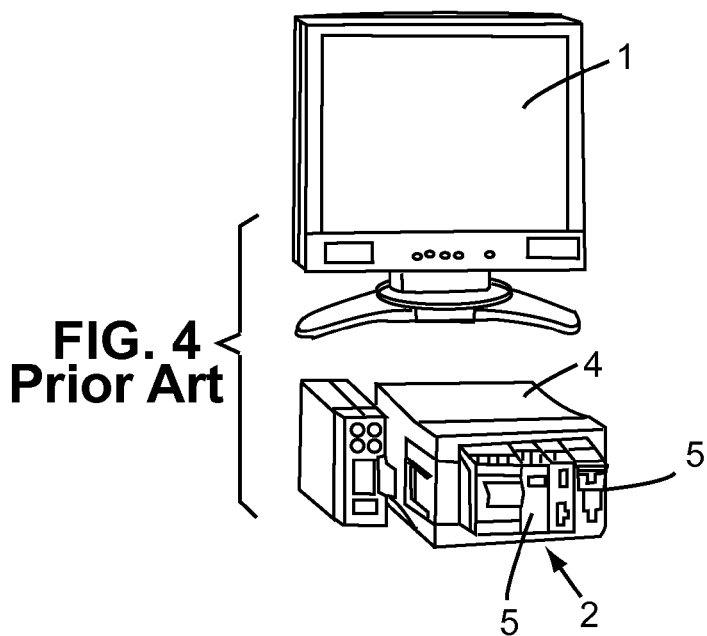
FIG. 4
Prior Art

PATIENT MONITOR

BACKGROUND OF THE INVENTION

The invention relates to a patient monitor comprising a display means and a parameter connection unit, the parameter connection unit comprising parameter connectors for connecting cables from a patient to the patient monitor.

Patients are monitored in hospitals with different types of patient monitors that gather vital data from the patient usually with measurement accessories that are connected to the monitor with cables. The data obtained is displayed on a display means, i.e. on a monitor screen together with other patient information or related information. The management of data is usually done with specific keys and control devices.

As an example of patient monitors known in the prior art Datex-Ohmeda Cardiocap/5 can be mentioned. This widely known device comprises a display means and a parameter connection unit, which is placed under the display means so that parameter connectors for connecting cables are facing forward. In this known device the parameter connection unit is an integral part of the monitor. Control keys for using the patient monitor are placed beside the display means so that the control keys are facing forward.

As there are different patient measurements needed for different cases there are also patient monitors where instead of integral, i.e. built-in parameter connection unit, a removable parameter module approach is chosen. With this modular monitor type, some or all of the parameters can be added to the monitor as separate parameter connection modules. As an example of said modular-type patient monitors known in the prior art Datex-Ohmeda S/5 Compact monitor can be mentioned. This known monitor comprises a display means with control keys, and a frame element placed behind the display element so that parameter connection modules can be removably inserted into the frame element. When the modules have been inserted into the frame element connectors for parameter cables are facing left behind the display means when normally looking at the display means.

It is also possible to build the parameter connection module frame as a separate unit from the display means. As an example of said monitor type Datex-Ohmeda S/5 Anesthesia Monitor can be mentioned.

The problems in the prior art can be described as follows. The needs to have the display means, i.e. the monitor screen and controls easily viewable and managed, and at the same time to be able to use the parameter cables and controls with eventual workspace constraints, i.e. it is difficult to place the monitor appropriately into a small space, and also easily to move or transport the monitor, are difficult to solve at the same time. The needs described above are currently approached with different methods, which can be described as follows.

BRIEF DESCRIPTION OF THE INVENTION

The module frame or built-in, i.e. integral parameter connectors can be built to face forward, either below, or on left/on right side of the screen. This brings the cable connectors to easier reach but at the same time limits the transportability because of the increased size that is needed around the display means and the cables getting on the way in transport situation. The arrangement described above is also not applicable to all work environments. An example of said solutions is Datex-Ohmeda Cardiocap/5 mentioned above.

The module frame or built-in parameter connectors can be positioned on the left or on the right side of the monitor to achieve compact size and easy transportability. This causes the aforementioned problems with difficult access to parameter cable connectors and some of the control keys. An example of said solutions is Datex-Ohmeda S/5 Compact Monitor mentioned above.

The parameter module frame element can be built as a separate unit from the display means and control devices. This arrangement makes the positioning of cable connectors quite free, especially in the limits of the size of the frame and display, helping to access all the needed functions but on the other hand this solution prohibits moving or transporting the monitor and that is why this solution is generally suitable only for areas with fixed equipment positioning. Also in those areas it may be difficult to arrange enough space that is needed for equipment consisting of several parts. An example of said solutions is Datex-Ohemda S/5 Anesthesia Monitor mentioned above.

The object of the invention is to provide a patient monitor that eliminates prior art problems. This is achieved with the present invention. The present invention is characterized in that the parameter connection unit is turnably pivoted to the display means.

The advantage of the invention is that the invention offers a flexible solution and therefore the invention can be adapted for wide variety of needs, for example the frame element can be adapted to several different types of parameter connection unit modules, recorder, memory equipment etc. The invention offers also improved workplace ergonomics in different type of environments.

BRIEF DESCRIPTION OF DRAWINGS

In the following the invention will be described in greater detail by means of the solutions shown in the accompanying drawing, in which FIG. 1 shows an example of the patient monitors known in the prior art, FIGS. 2 and 3 show a second example of the patient monitors known in the prior art, FIG. 4 shows a third example of the patient monitors known in the prior art.

DETAILED DESCRIPTION OF THE INVENTION

Figure 5:
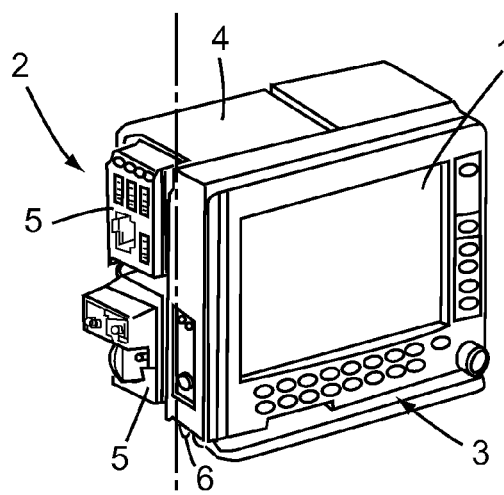
FIGS. 5-8 show one embodiment of the invention in different situations.

FIG. 1 shows an example of the patient monitors widely known in the field, namely Datex-Ohmeda Cardiocap/5 patient monitor. Reference number 1 shows a display means, i.e. a monitor screen. Reference number 2 shows a parameter connection unit comprising several parameter connectors for connecting cables from a patient to the patient monitor. Cables and other accessories relating to cables are elements that are quite familiar for a person skilled in the art, and therefore said details are not shown in FIG. 1. Reference number 3 shows control keys for using the monitor. At least some of the control keys can also be placed next to the parameter cable connectors.

As shown in FIG. 1 the parameter connection unit 2 is an integral part of the monitor and the parameter connectors are facing forward. This arrangements lead to problems described earlier in the text.

FIGS. 2 and 3 show another example of the monitors widely known in the field, namely Datex-Ohmeda S/5 Compact Monitor patient monitor. Reference number 1 shows a display means, and reference number 2 show a parameter connection unit. In this device the parameter connection unit comprises a frame element 4 and parameter connection unit modules 5 into which parameter connectors have been placed. The parameter connection unit modules 5 can be removably inserted to the frame element 4 as shown in FIGS. 2 and 3. Different modules can be used according to the existing needs. Reference number 3 shows control keys for the monitor. FIG. 3 shows also how cables can be connected to the parameter connectors.

As shown in FIGS. 2 and 3 the parameter connection unit 2 is placed on the left side of the monitor so that the parameter connectors are facing left. The parameter connection unit 2 can however also be placed on right side of the monitor so that the parameter connectors are facing to right. FIGS. 2 and 3 show a device in which removable modules are used. It is also possible to use a construction in which the parameter connection unit 2 is placed as shown in FIG. 3 but so that instead of modules an integral structure is used.

Sideways facing parameter connectors lead to problems relating to difficult access to the connectors as described earlier in the text.

FIG. 4 shows a third example of the monitors widely known in the prior art, namely Datex-Ohmeda S/5 Anesthesia Monitor patient monitor. Reference number 1 shows a display means, and reference number 2 shows a parameter connection unit. Reference number 4 shows a frame element and reference number 5 show modules inserted in the frame element 4. FIG. 4 shows also additional parameter connection unit module that can be inserted into the frame element 4. In this known device the display and the parameter connection unit have been built as separate units. This arrangement leads to problems relating to moving or transporting the equipment as described earlier in the text.

As told before the devices known in the prior art have problems and before the invention there is not available a patient monitor that combined the ergonomic needs in all different situations.

FIGS. 5-8 show one embodiment of the present invention. In FIGS. 5-8 same reference numbers are used to show corresponding elements as shown in FIGS. 1-4, i.e. reference number 1 shows a display means and reference number 2 shows a parameter connection unit. Reference number 3 shows control keys for using the monitor.

Figure 6:
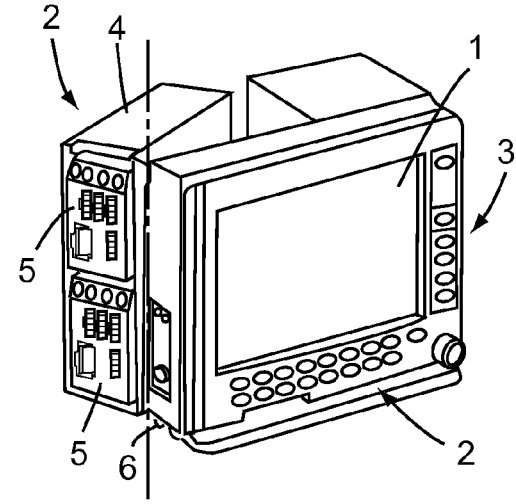
Figure 7:
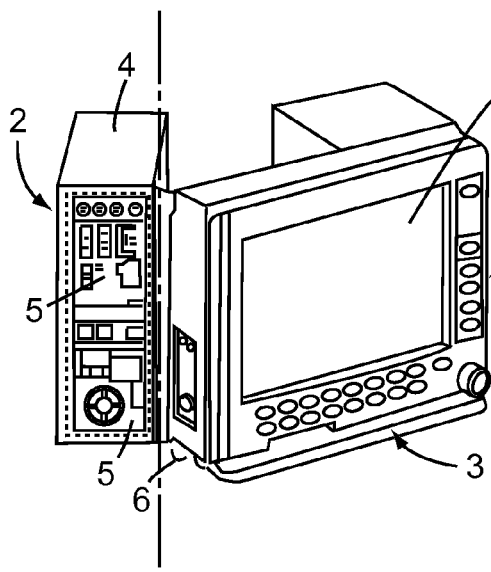
Figure 8:
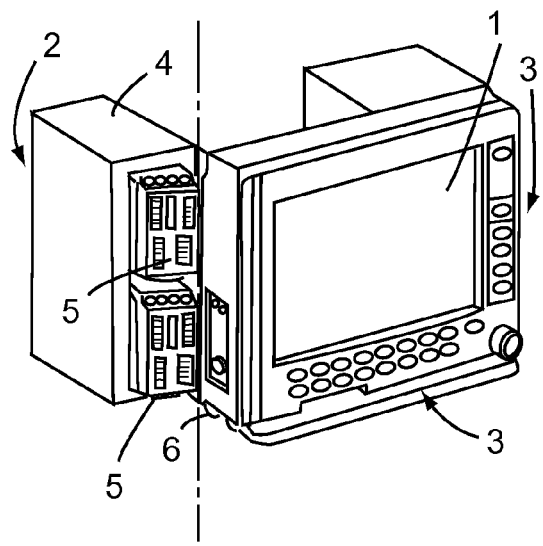

The essential idea in the present invention is that the parameter connection unit 2 is turnably pivoted to the display means. Said idea can be clearly seen when looking at FIGS. 5-8, which show the parameter connection unit 2 in different positions. FIG. 5 shows the parameter connection unit in its fully closed position and FIG. 8 show the parameter connection unit 2 in its fully open position. FIGS. 6 and 7 show the parameter connection unit in the position between said fully closed and fully open positions.

It is easy to see that FIGS. 5-8 show that the parameter connection unit 2 is pivoted so that the parameter connection unit 2 can be turned around a pivot axle from a position in which the parameter connectors are facing essentially on the side surfaces of the display means 1 to another position in which the parameter connectors are facing at least partly on the front surface of the display means 1. The position in which the parameter connectors are facing essentially on the side surface of the display means 1 is the fully closed position mentioned above and shown in FIG. 5. The position in which the parameter connectors are facing at least partly on the front surface of the display means 1 is the fully open position mentioned above and shown in FIG. 8. The pivot axle mentioned above is shown in FIGS. 5-8 with dotted lines. The parameter connection unit 2 can be arranged to turn essentially at least about 45 degrees from the fully closed position.

It is further advantageous if the parameter connection unit 2 can be turned essentially about 60 degrees from the fully closed position. Perhaps the best embodiment is the one in which the parameter connection unit 2 can be turned essentially about 90 degrees from the fully closed position.

The parameter connection unit 2 can be provided with a locking means 6 so that the parameter connection unit 2 can be securely locked at least to one position. The operation principle of the locking means 6 can be based on friction principle, snap-on principle, tap-and-hole principle or any other principle per se. The parameter connection unit 2 can be locked into fully closed position, fully open position and also in-between positions to accommodate different workplaces.

The pivot axle around which the parameter connection unit 2 turns can be vertical as shown in FIGS. 5-8. This is however not the only possibility but said pivot axle can also be for example horizontal, i.e. the parameter connection unit 2 can be placed under the display means and arranged so that it can be turned around a horizontally placed pivot axle to a fully open position etc. The pivot axle can also run in any direction between vertical and horizontal directions if said directions are found advantageous in certain circumstances. The angle of the pivot axle can be for example 30, 45 or 60 degrees counted from horizontal or vertical direction.

SUMMARY OF THE INVENTION

The basic idea of the invention can be materialized in various ways. It is for example quite possible to design the parameter connection unit 2 so that said unit comprises a frame element 4 into which parameter connection unit modules 5 having different parameter connectors can be removably inserted. This arrangement is shown in FIGS. 5-8. It is possible also to design the frame element 4 according to the types of parameter connection units modules 5 needed for certain situations or according to the needs presented by the customer. It is however also within the spirit of the invention to form the parameter connection unit 2 so that modules are not used but so that for example the parameter connection unit 2 is formed as an integrated structure, i.e. so that said modules are not used but the parameter connectors form an integral part with the frame structure.

The embodiments of the invention described above are by no means intended to restrict the invention, but the invention can be freely modified within the scope of the claims. Accordingly, it is apparent that the patient monitor of the invention and its details do not necessary have to be as described above and in the Figures, but other solutions are also feasible.

What is claimed is:

1. A patient monitor, comprising:
a display unit comprising a front surface with a monitor disposed thereon, a rear surface opposite the front surface, and a plurality of outer peripheral surfaces, each of said outer peripheral surfaces extending between the front surface and the rear surface, the plurality of outer peripheral surfaces each comprising a front edge that intersects with a respective edge of the front surface and a rear edge spaced away from the front surface that intersects with a respective edge of the rear surface;
a parameter connection unit comprising a frame element and a module comprising a parameter connector configured to connect to cables from measurement accessories that gather vital data from a patient, wherein the module is removably inserted into the frame element so that the parameter connector is positioned about a first side surface of the frame; and a pivot axle extending along the rear edge of one of the outer peripheral surfaces, the pivot axle configured to couple the display unit to the frame element to permit the parameter connection unit to be rotatable about the pivot axle relative to the display unit between a first position where the parameter connection unit is substantially flush against the rear surface of the display unit, and a second position about 90 degrees from the first position, wherein the display is completely visible and unobstructed when the parameter connection unit is in the first position, the second position, and any intermediate position between the first and the second position.

2. The patient monitor according to claim 1, wherein the first side surface of the frame of the parameter connection unit is (i) approximately perpendicular to the front surface when the parameter connection unit is in the first position, and (ii) approximately parallel to the front surface when the parameter connection unit is in the second position.

3. The patient monitor according to claim 1, wherein the parameter connection unit comprises a locking means so that the parameter connection unit can be locked at least to one position relative to the display unit.

4. The patient monitor according to claim 1, wherein the display unit rests on one of the outer peripheral surfaces and the pivot axle is approximately perpendicular to the peripheral surface on which the display unit rests.

5. The patient monitor according to claim 1, wherein the display unit rests on one of the outer peripheral surfaces and the pivot axle is approximately parallel to the peripheral surface on which the display unit rests.

6. The patient monitor according to claim 1, wherein the frame element is configured for different types of the parameter connection unit modules.

* * * * *